(12) United States Patent
Brundle et al.

(10) Patent No.: US 7,338,260 B2
(45) Date of Patent: Mar. 4, 2008

(54) SYSTEM AND METHOD FOR CONTROLLING CURRENT PROVIDED TO A STEPPING MOTOR

(75) Inventors: Alan Brundle, Barrington, IL (US); Tim Allen, Poole (GB); Son Dao, Arlington Heights, IL (US)

(73) Assignee: Baxter International Inc., Deerfield, IL (US)

( * ) Notice: Subject to any disclaimer, the term of this patent is extended or adjusted under 35 U.S.C. 154(b) by 533 days.

(21) Appl. No.: 10/802,180

(22) Filed: Mar. 17, 2004

(65) Prior Publication Data

US 2005/0206340 A1    Sep. 22, 2005

(51) Int. Cl.
*F04B 49/06* (2006.01)
*F04B 49/00* (2006.01)
*A61M 1/00* (2006.01)

(52) U.S. Cl. .................. 417/44.2; 417/43; 417/45; 417/12; 604/153

(58) Field of Classification Search ............ 417/45, 417/53, 12, 44.2, 32, 43, 479; 604/153; 702/45, 702/50, 127
See application file for complete search history.

(56) References Cited

U.S. PATENT DOCUMENTS

| | | | |
|---|---|---|---|
| 3,885,210 A | 5/1975 | Burnett | |
| 4,431,955 A | 2/1984 | Faedi et al. | |
| 4,683,408 A | 7/1987 | Inoue et al. | |
| 4,751,445 A | 6/1988 | Sakai | |
| 4,838,856 A * | 6/1989 | Mulreany et al. ............ 604/65 |
| 4,855,660 A * | 8/1989 | Wright et al. ............... 318/696 |
| 4,961,037 A | 10/1990 | Orii et al. | |
| 5,008,607 A | 4/1991 | Ono et al. | |
| 5,198,741 A | 3/1993 | Shinada et al. | |
| 5,206,571 A | 4/1993 | Burri | |
| 5,216,345 A | 6/1993 | Eyerly | |
| 5,355,067 A | 10/1994 | Tabuchi | |
| 5,574,351 A | 11/1996 | Jacobson et al. | |
| 5,583,410 A | 12/1996 | Jacobson et al. | |
| 5,710,499 A | 1/1998 | Carvajal | |
| 5,739,661 A | 4/1998 | Wakuda | |
| 5,838,132 A | 11/1998 | Tanaka | |
| 5,844,394 A | 12/1998 | Mushika et al. | |
| 5,914,579 A | 6/1999 | Komm | |
| 5,932,987 A | 8/1999 | McLoughlin | |
| 5,963,006 A | 10/1999 | Otani | |
| 5,982,134 A | 11/1999 | Tanaka | |
| 6,046,567 A | 4/2000 | Hayes | |
| 6,121,745 A | 9/2000 | Komm | |
| 6,124,696 A | 9/2000 | Rademacher et al. | |
| 6,150,789 A | 11/2000 | Pulford, Jr. | |
| 6,208,107 B1 * | 3/2001 | Maske et al. ............... 318/685 |
| 6,285,156 B1 | 9/2001 | Hartzsch | |

(Continued)

*Primary Examiner*—Devon C. Kramer
*Assistant Examiner*—Jessica L Frantz
(74) *Attorney, Agent, or Firm*—Austin J. Foley; Bell, Boyd & Lloyd LLP

(57) ABSTRACT

A system and method is disclosed for controlling the input electrical current to an infusion pump stepper motor based on predetermined torque requirements. The system can include a motor controller and a non-volatile memory containing expected load torque values throughout a pump cycle. Responsive to the expected load torque values, the motor controller provides the stepper motor with a varying electrical current for overcoming load torque at each point in the pumping cycle. Additional factors can also be considered for varying the electrical current. These factors include, but are not limited to, temperature, pressure, and elapsed operating time.

26 Claims, 4 Drawing Sheets

U.S. PATENT DOCUMENTS

| | | |
|---|---|---|
| 6,394,771 B2 * | 5/2002 | Butterfield ............... 417/477.1 |
| 6,441,579 B1 | 8/2002 | Van Lydegraf et al. |
| 6,459,229 B1 | 10/2002 | Kawanabe |
| 6,462,503 B1 | 10/2002 | Narazaki |
| 6,509,709 B2 | 1/2003 | Kubozuka et al. |
| 6,573,680 B2 | 6/2003 | Sasama |
| 6,659,980 B2 * | 12/2003 | Moberg et al. ............. 604/154 |
| 2002/0171297 A1 | 11/2002 | Talbot et al. |
| 2003/0225396 A1 * | 12/2003 | Cartledge et al. ........ 604/890.1 |
| 2003/0235409 A1 * | 12/2003 | Harriman et al. ........... 388/804 |

* cited by examiner

SYSTEM AND METHOD FOR CONTROLLING CURRENT PROVIDED TO A STEPPING MOTOR

FIELD OF THE INVENTION

This invention relates generally to a system and method for controlling the electrical current provided for driving a stepper motor. More particularly, the invention relates to a system and method for providing a variable electrical current for driving a stepper motor used within a medical delivery device such as an infusion pump.

BACKGROUND OF THE INVENTION

A stepper motor is a type of electric motor that moves in increments, or steps, rather than turning smoothly as a conventional electric motor does. Typically, the size of the increment is measured in degrees and can vary depending upon the application. For instance, increments can be 0.9 or 1.8 degrees, with 400 or 200 increments thus representing a full circle. Moreover, the speed of the motor is determined by the time delay between each incremental movement.

Inside the typical stepper motor, sets of coils produce magnetic fields that interact with the fields of permanent magnets. The coils are switched on and off in a specific sequence to cause the motor shaft to turn through the desired angle. The typical motor can operate in either direction (clockwise or counterclockwise). When the coils of a stepper motor receive current, the rotor shaft turns to a certain position and then stays there unless or until different coils are energized. Unlike a conventional electric motor, the stepper motor resists external torque applied to the shaft once the shaft has come to rest with current applied. This resistance is typically called holding torque.

The holding torque of a stepper motor is not constant with position but varies as the shaft moves from one full step position to the next. This variation is caused by the detent torque, which adds and subtracts from the electrically induced torque as the shaft of the motor moves. The detent torque can be approximated by a sinewave torque that repeats every full step of the motor. The magnitude of the resultant current determines the torque available from the motor.

A stepper motor is also characterized by load torque. In order to avoid loss of step, sufficient electrical current must be applied to overcome the load torque. However, the load torque can vary considerably over a pumping cycle when the motor is used within an infusion pump. Loss of step may result in a motor stall. To recover from motor stall, the motor may need to be restarted at a lower speed than that at which the stall occurred, and then accelerated to the original speed. This restart procedure requires a higher current to produce the torque. This higher torque wastes energy.

As will be appreciated by those having skill in the art, the full-step resolution of the stepper motor may be increased by applying currents to the motor coils in such proportions that the motor is positioned at some point between the full-step detent positions. Thus, in a two-phase stepper motor, energizing both coils will result in the motor being positioned halfway between the adjacent full-step positions. This is referred to as half-stepping. A full step may be further subdivided by applying a current which is the sine of the required position to one phase, and the cosine of the required position to the other phase. This is referred to as microstepping. The motor torque is a function of the vector sum of the currents applied to each phase, irrespective of the type of drive.

As indicated previously, one use of a stepper motor is to control an infusion pump such as a volumetric or peristaltic pump. Infusion pumps are used to automatically administer liquid medicants to patients. The liquid medicant is supplied from a source of medicant and delivered to the patient via a catheter or other injection device.

A common type of volumetric pump for intravenous fluids produces a peristaltic flow such as that disclosed by U.S. Pat. No. 5,842,841, incorporated herein by reference. Within this type of pump, a plastic tube leading from the bag or bottle on the drip stand to the intravenous needle (i.e. the 'giving set' or 'drip-set') passes through a special gate in which it is occluded between a row of 'fingers' which are moved by a cam mechanism to squeeze the closed point forward.

However, the tube is repeatedly deformed in an identical manner, thereby over the course of time destroying the elastic recovery properties of the tube so that the tube maintains a compressed aspect. This destruction of the elastic recovery properties of the tube results in the volumetric output of the pump changing markedly over time.

Today, there is a desirability of operating infusion pumps and other medical devices using a battery power source. Accordingly, conservation of power is an important feature for operating battery powered medical devices over a prolonged period of time.

SUMMARY OF THE INVENTION

The present invention is a system and method for controlling the input current to an infusion pump stepper motor based on predetermined torque requirements. The system can include a motor controller and a non-volatile memory containing expected load torque values throughout a pump cycle. Responsive to the expected load torque values, the motor controller provides the stepper motor with a varying electrical current for overcoming load torque at each point in the pumping cycle. Additional factors can also be considered for varying the electrical current. These factors include, but are not limited to, temperature, pressure, and elapsed operating time.

Other features and advantages of the invention will be apparent from the following specification taken in conjunction with the following drawings.

DETAILED DESCRIPTION OF THE PREFERRED EMBODIMENT

Figure 1:
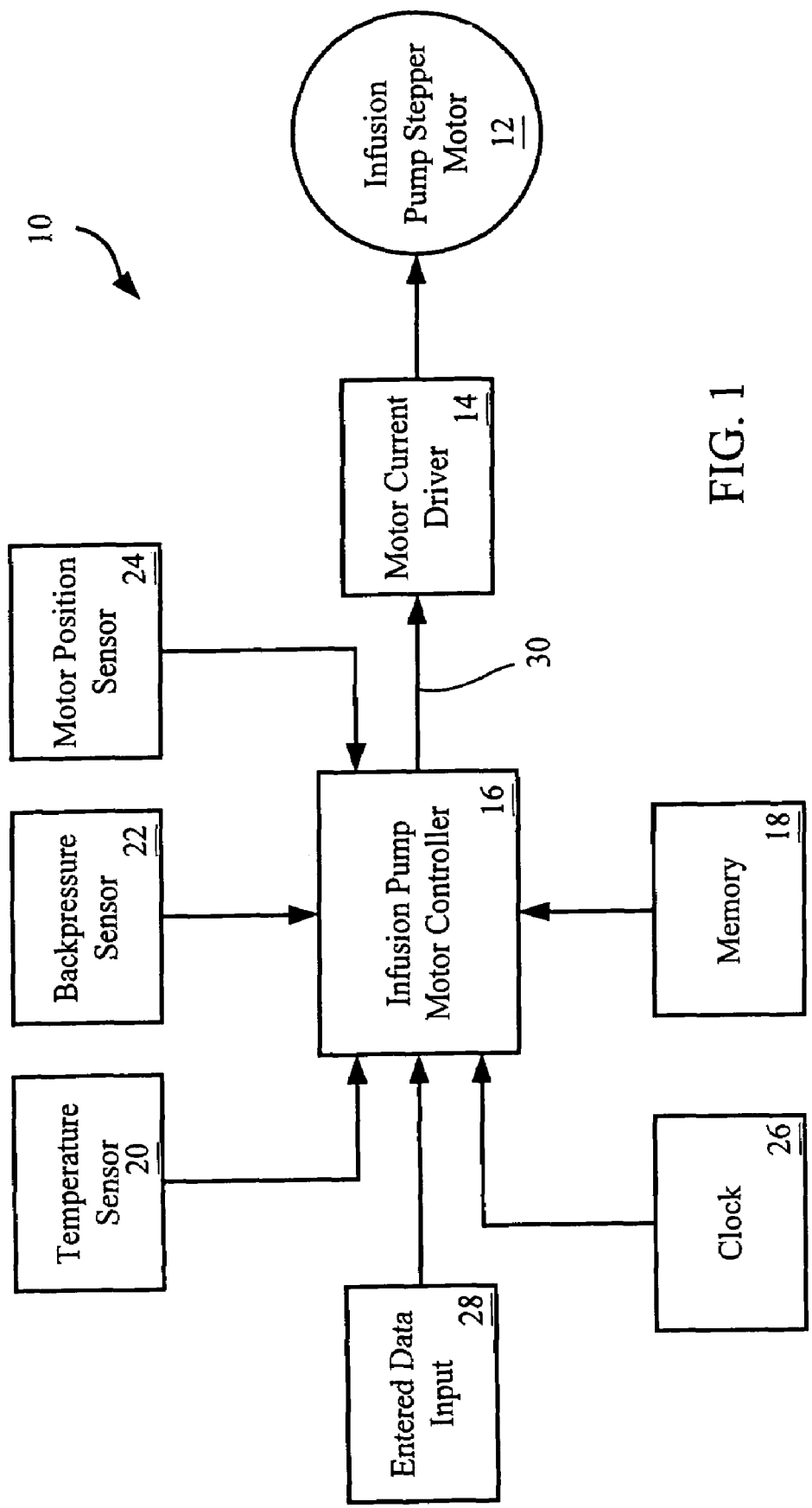
FIG. 1 is a simplified electrical schematic, in block diagram form, of a system for controlling the electrical current provided to a stepper motor in accordance with the present invention.

While this invention is susceptible of embodiments in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated.

Turning to FIG. 1, a simplified electrical schematic, in block diagram form, is depicted of a system for controlling the electrical current provided to a stepper motor in accordance with the present invention. The system 10 includes a stepper motor 12, a motor current driver 14, an infusion pump controller 16, a memory 18, a temperature sensor 20, a backpressure sensor 22, a motor position sensor 24, a clock 26, a data input 28, and a power source (not shown). As will be appreciated by those having ordinary skill in the art, each block within FIG. 1 includes electrical circuitry for performing a function or task as herein described.

In an embodiment, the stepper motor 12 is a conventional stepper motor used in an infusion pump. Accordingly, the stepper motor 12 is operably connected to one or more mechanical structures (not shown) for mechanically controlling the delivery of fluid to a patient (not shown). As will be appreciated by those having ordinary skill in the art, the mechanical structures used within such infusion pumps are well known in the art. Therefore, such structures are not discussed further herein.

Electrical current for driving the stepper motor 12 is provided by the motor current driver 14 of conventional design. In response to the motor drive signal 30 provided by the motor controller 16, the motor current driver 14 supplies electrical current for driving the stepper motor 12.

The motor drive signal 30 can be a digital or analog signal containing information or data regarding the amount of electrical current to be supplied by the motor current driver 14 for driving the stepper motor 12. For instance, the motor drive signal 30 can be a four bit digital signal wherein: a binary "0" results in the current driver 14 providing no electrical current to the stepper motor 12; a binary "1111" (i.e., decimal 15) results in the current driver providing maximum electrical current to the stepper motor; and binary values between "0" and "15" result in the current driver providing constant incremental increases or varying incremental increases in the electrical current supplied to the stepper motor 12. In another example, the motor drive signal 30 can be a 0 to 5 volt analog signal wherein: about 0 volts results in the current driver 14 providing no electrical current to the stepper motor 12; a voltage of about 5 volts results in the current driver providing maximum electrical current to the stepper motor; and analog values between about 0 and 5 volts result in the current driver 14 providing corresponding increases or decreases in the electrical current provided to the stepper motor 12.

As will be appreciated by those having ordinary skill in the art, the current driver 14 is operably connected to a conventional power supply (not shown) for supplying electrical current to the stepper motor 12. In turn, the power supply can be operably connected to an alternating voltage source (e.g., a conventional 120 VAC wall socket), a battery, or the like.

In response to one or more inputs, the motor controller 16 provides the motor driver 14 with the motor drive signal 30. These inputs to the motor controller 16 can include, but are not limited to, the data provided by: memory 18, temperature sensor 20, backpressure sensor 22, motor position sensor 24, clock 26, and input 28.

In response to the inputs, the motor controller 16 operates the stepper motor 12 with sufficient electrical current to avoid a loss of step, and thus possibly a motor stall. However, the amount of electrical current provided to the stepper motor 12 by the motor controller 16 is based on need (i.e., the electrical current is variable), rather than just being set at a constant amperage.

When and how the stepper motor 12 operates is determined by the data input 28 typically entered manually or by remote means. Accordingly, the data input 12 can consist of data or information regarding, for instance, the cycle times and flow rate to be administered by the infusion pump.

Generally, the memory 18 provides the motor controller 16 with data for characterizing the load torque throughout the pumping cycle. In particular, the memory 18 includes data corresponding to the amount of electrical current that the stepper motor 12 should receive based on one or more variables or factors. As described below, these variables or factors can include temperature, backpressure, motor position, and operating duration. Accordingly, the motor controller receives information or data regarding the variables, the motor controller then compares or processes the received information with the data provided by the memory 18, and then generates a corresponding motor drive signal 30 for operating the stepper motor 12.

In an embodiment, the temperature sensor 20 is conventional in operation and design. The sensor 20 provides the motor controller 16 with information or data regarding the ambient temperature about the system 10. As will be appreciated by those having ordinary skill in the art, the typical tubing used within an IV set for applying medication intravenously will become more difficult for an infusion pump to manipulate as temperature decreases. Thus, in response to the data provided by the memory 18 and the temperature sensor 20, the motor controller 16 increases the amount of electrical current provided to the stepper motor 12 as the temperature decreases. Likewise, the motor controller 16 decreases the amount of electrical current provided to the stepper motor 12 as the temperature increases. Moreover, on startup of the pump, the motor controller 16 provides electrical current to operate the stepper motor 12 wherein the amount of electrical current is based, at least in part, on the information received by the temperature sensor 20.

The backpressure sensor 22 is conventional in operation and design. The sensor 22 provides the motor controller 16 with information or data regarding the backpressure (e.g., distal pressure) resisting the forward pressure generated by the infusion pump in applying medication intravenously. Accordingly, in response to the data provided by the memory 18 and the backpressure sensor 22, the motor controller 16 increases the amount of electrical current provided to the stepper motor 12 as the backpressure increases. Similarly, the motor controller 16 decreases the amount of electrical current provided to the stepper motor 12 as the backpressure decreases. Further, on startup of the pump, the motor controller 16 provides electrical current to operate the stepper motor 12 wherein the amount of electrical current is based, at least in part, on the information received by the backpressure sensor 22.

The motor position sensor 24 is conventional in operation and design. The motor position sensor 24 provides the motor controller 16 with information or data regarding the position of the stepper motor 12. As such, in response to the data provided by the memory 18 and the position sensor 24, the motor controller 16 increases or decreases the amount of electrical current provided to the stepper motor 12 based upon increases or decreases, respectively, in the amount of holding torque. Also, on startup of the pump, the motor controller 16 provides electrical current to operate the stepper motor 12 wherein the amount of electrical current is based, at least in part, on the information regarding the motor position.

The clock 26 provides the motor controller 16 with information or data for indicating or measuring time. As will be appreciated by those having ordinary skill in the art, the elastic recovery properties of the IV tubing decrease as the tubing is repeatedly deformed by the infusion pump during intravenous medication delivery. Thus, the tubing is easier for the infusion pump to manipulate over time. However, the energy efficiency of stepper motors typically decreases as the motors age.

In response to the data provided by the memory 18 and the clock 26, the motor controller 16 decreases the amount of electrical current provided to the stepper motor 12 as the tubing installed within the pump ages. However, the motor controller 16 increases the amount of electrical current provided to the stepper motor 12 as the stepper motor ages.

Although the clock is shown in FIG. 1 as a separate block from the motor controller 16, the clock can be integrated within the motor controller. For instance, the motor controller can be a central processing unit or a microcontroller having an internal clock. Moreover, it is preferred that the memory 18 is non-volatile and can be separate from the motor controller, as shown in FIG. 1, or integrated within the motor controller.

In an embodiment, the electrical current provided to the stepper motor can be expressed as the following formula:

> Total Electrical Current Provided To Stepper Motor=Initial Operating Electrical Current Based On Entered Data Input 28+Incremental Increase Or Decrease In Electrical Current Based On Data From Temperature Sensor 20+Incremental Increase Or Decrease In Electrical Current Based On Data From Backpressure Sensor 22+Incremental Increase Or Decrease In Electrical Current Based On Data From Motion Position Sensor 24+Incremental Increase Or Decrease In Electrical Current Based On Elapsed Time That Tubing Has Been Manipulated By The Motor 12+Incremental Increase Or Decrease In Electrical Current Based On Elapsed Time That Stepper Motor 12 Has Been Operated.

However, as will be appreciated by those having ordinary skill in the art, any of the above factors within the above formula can be modified and/or omitted.

Figure 2:
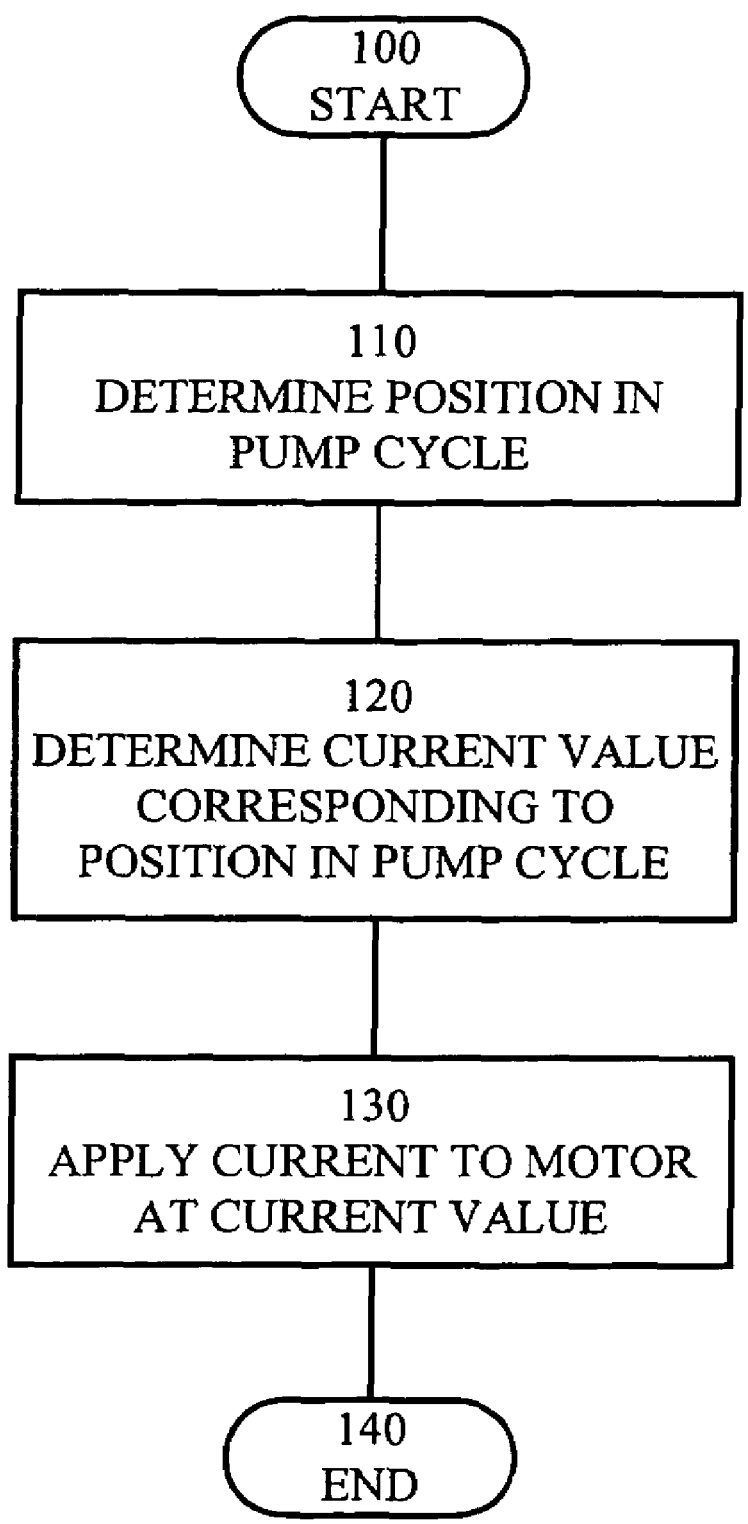
FIG. 2 is a simplified flowchart illustrating a method for controlling the electrical current provided to a stepper motor in accordance with the present invention.

FIG. 2 is a simplified flowchart illustrating a method in accordance with the present invention. As shown in FIG. 2, the method begins at step 100, and continues to step 110, in which a position in the pump cycle is determined. In one exemplary embodiment, the position in the pump sequence is a temporal coordinate relative to the start of a pump cycle. In another exemplary embodiment, the position in the pump cycle is a temporal coordinate relative to the start of a complete pump cycle. In another exemplary embodiment, the position in the pump cycle is a temporal coordinate relative to the beginning of the use of an IV set for a single session. In another exemplary embodiment, the position in the pump cycle is a temporal coordinate relative to the beginning of use of the device.

Next, at step 120, an electrical current value is determined corresponding to the position in the pump sequence. In one embodiment, the electrical current value is stored in a database that relates the position in the pump sequence to a corresponding electrical current value. As indicated previously, the database can be stored in a memory provided within a medical pump.

Next, at step 130, electrical current is applied to the stepper motor at the value determined at step 120. Finally, at step 140, the method ends.

Figure 3:
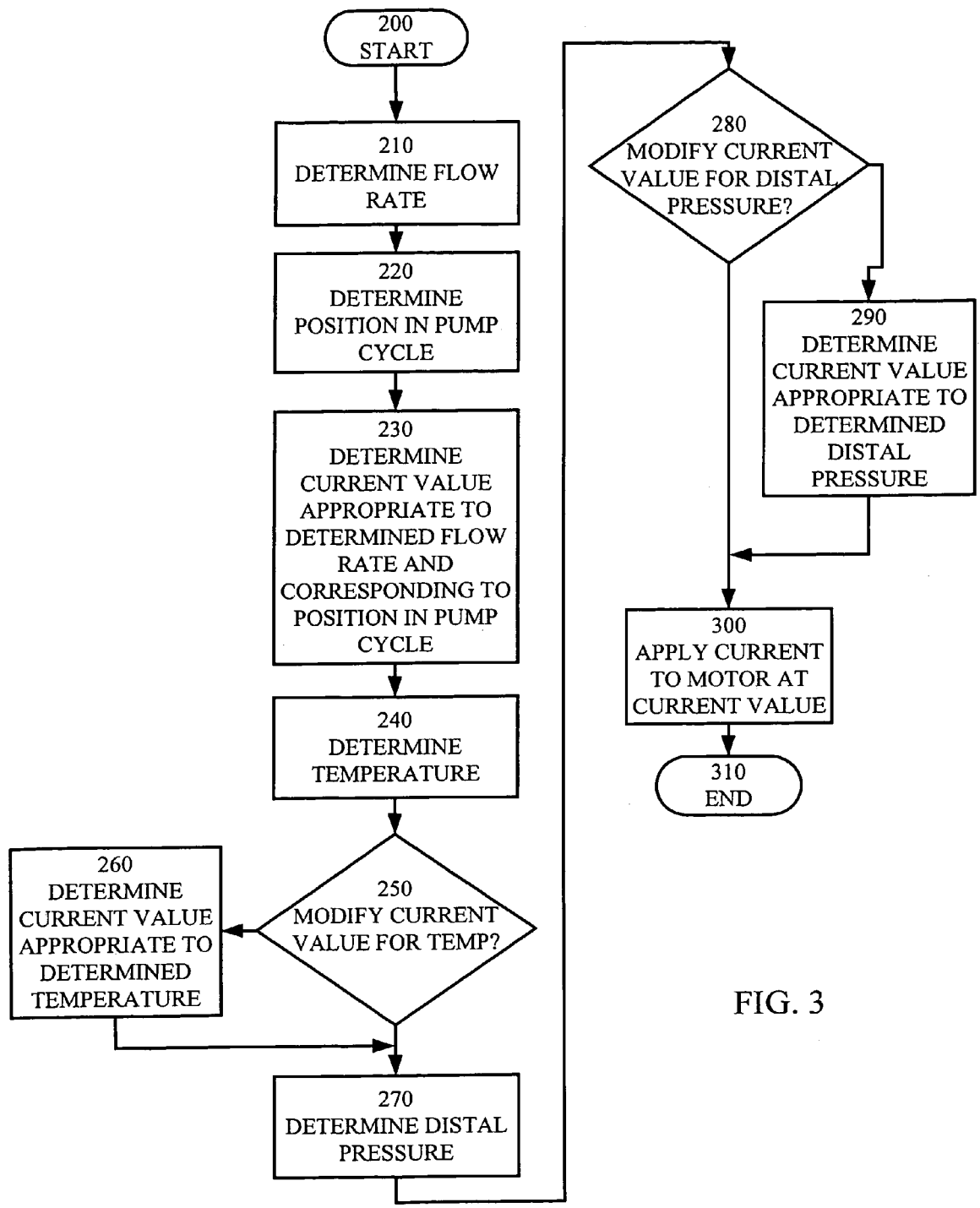
FIG. 3 is a simplified flowchart illustrating another embodiment of a method for controlling the electrical current provided to a stepper motor in accordance with the present invention.

FIG. 3 is a simplified flowchart illustrating another embodiment of a method in accordance with the present invention. As shown in FIG. 3, the method begins at step 200, and continues to step 210, in which a flow rate is determined. The determined flow rate is a measure of the instantaneous flow of liquid through a pump being driven by a stepper motor. In one exemplary embodiment, the determined flow rate is stored in a computer register or memory for later use. In another exemplary embodiment, the determined flow rate is stored in a database for later use.

Next, at step 220, similar to step 110 of FIG. 2, a position in the pump cycle is determined. Next, at step 230, an electrical current value is determined based on two parameters. The first parameter is the position in the pump cycle as determined in step 220. The second parameter is the flow rate determined in step 210. In one exemplary embodiment, the position in the pump cycle is retrieved from a database table stored in a computer or system memory.

Next, at step 240, the temperature of the IV set is determined or approximated. Then, at decision step 250, a determination is made whether the electrical current value determined in step 230 is to be modified according to the temperature determined in step 240. In one embodiment, this determination is made based on the results of an algorithm relating a electrical current value at the actual temperature reading to the electrical current value at a standard temperature reading. In another embodiment, this determination is made based on values stored in one or more database tables relating temperature to electrical current values.

If the electrical current value is to be changed based on the determined temperature in step 240, then a change in the electrical current value is determined in step 260, and then processing continues to step 270. However, if the electrical current value is not to be changed based on the determined temperature in step 240, then processing continues directly to step 270.

At step 270, the distal pressure is determined. In one embodiment, distal pressure is the backpressure resisting the forward pressure generated by the pump. Processing then continues to step 280 wherein a determination is made whether the electrical current value is to be further modified according to the distal pressure determined in step 270. In one embodiment, this determination is made based on the results of an algorithm relating an electrical current value at the distal pressure reading to the electrical current value at a standard distal pressure reading. In another embodiment, this determination is made based on values stored in one or more database tables relating distal pressure to electrical current values.

If the electrical current value is to be changed based on the determined pressure in step 270, then processing continues at step 290. In step 290, the electrical current value is set to a current value appropriate to all determined values including distal pressure. Processing then continues at step 300. However, if the electrical current value is not to be changed based on the determined temperature in step 270, then processing continues directly to step 300. At step 300, electrical current at the value determined at one or more of steps 230, 260 or 290 is applied to the stepper motor. Finally, at step 310, the method ends.

Figure 4:
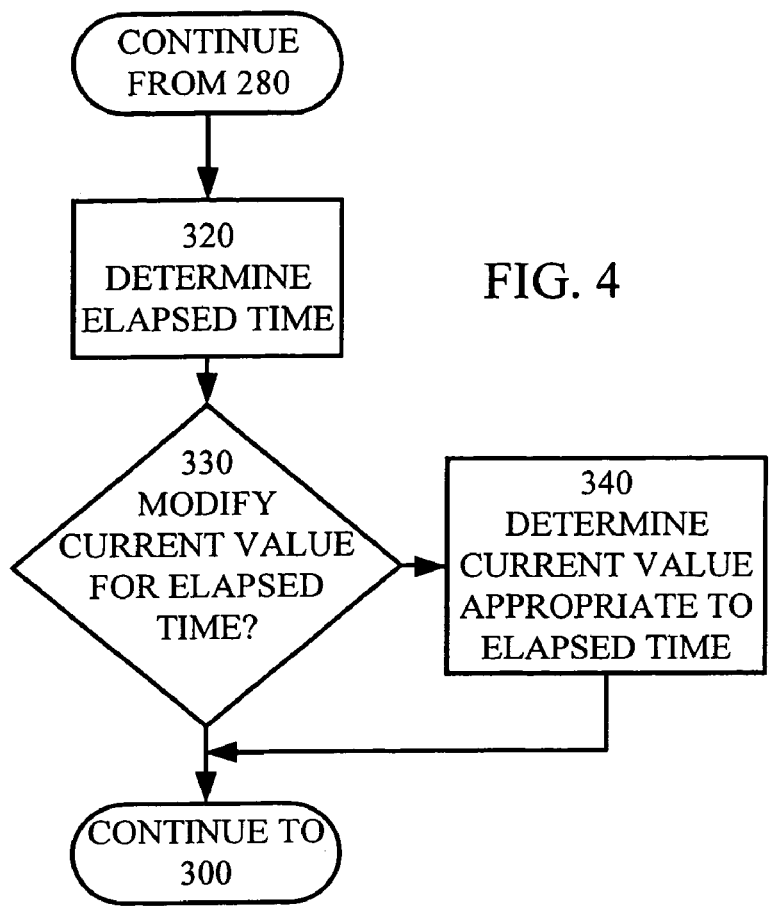
FIG. 4 is a simplified flowchart illustrating a modification to the method depicted in FIG. 3; and, FIG. 5 is a simplified flowchart illustrating yet another modification to the method depicted in FIG. 3.

FIG. 4 is a simplified flowchart illustrating a modification to the method depicted in FIG. 3. Within FIG. 4, the electrical current value determined in the method of FIG. 3 is further determined with reference to the elapsed time of a volumetric infusion pump motor session.

Specifically, as stated previously, the method of FIG. 3 includes steps wherein: at step 210 the flow rate is determined; at step 220 the position of the motor in the pumping cycle is determined; at step 240 the temperature of the IV set is determined or approximated; and, at step 270 the distal pressure is determined. Next, at step 240, a position in the pump cycle is determined. Next, at step 250, a current value is determined based on the position in the pump cycle as determined in step 240, as well as the flow rate as determined in step 210.

Next, decisions are made wherein: at step 230 an electrical current value is determined based upon the flow rate and the position of the stepper motor; at step 250 a determination is made whether the electrical current value is to be modified based on the temperature information; and, at step 280 a determination is made whether the current value is to be modified based on the pressure information.

In FIG. 4, an additional step 320 is provided wherein the elapsed time of a volumetric infusion pump motor session is determined. In one embodiment, a microprocessor-based clock is polled to determine elapsed time. Operation continues at decision step 330, in which a determination is made whether to modify the electrical current value to account for any changes in torque due to time-related factors. If a determination is made in step 330 that the electrical current should be modified, then processing continues at step 340. Accordingly, at step 340, the current value is set to a current value appropriate to all determined values, including elapsed time. In one embodiment, the determination of the current value appropriate to elapsed time is determined by applying a time-dependent algorithm to a predetermined current value appropriate to all other determined values. In another embodiment, the determination of the current value appropriate to elapsed time is determined by querying a database containing a table relating current values to elapsed time. Processing then continues at step 300.

If a determination is made at step 330 that the electrical current should not be modified, then processing continues at step 300. At step 300, current at the current value determined by the method of FIGS. 3 and 4 is applied to the stepper motor. Finally, at step 310, the method ends.

Figure 5:
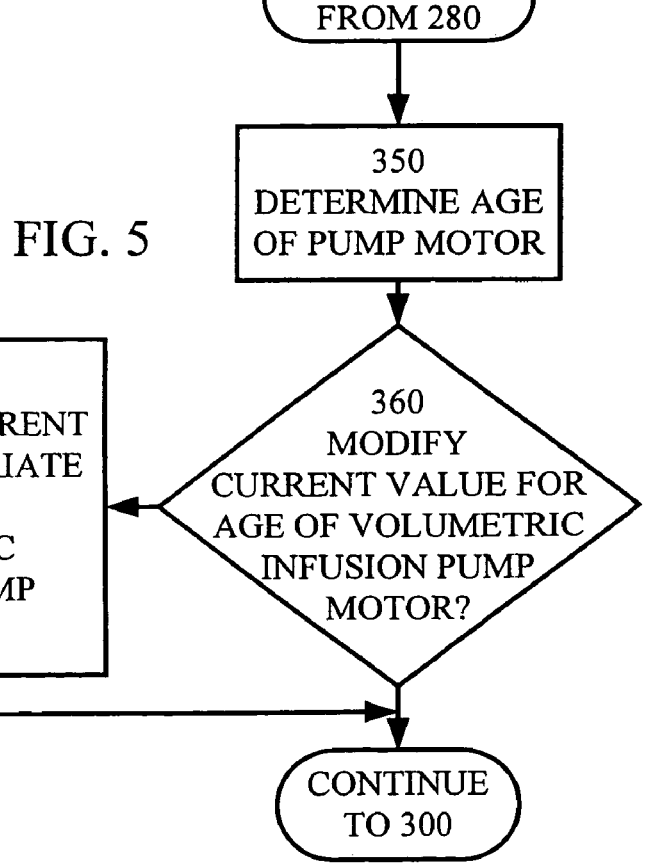

FIG. 5 is a simplified flowchart illustrating yet another modification to the method illustrated in FIG. 3. Within FIG. 5, the electrical current value determined in the method of FIG. 3 is further determined with reference to the age of a volumetric infusion pump motor.

Specifically, within FIG. 5, an additional step 350 is provided wherein the age of a volumetric infusion pump motor is determined. In one embodiment, the age of a volumetric infusion pump motor is a sum of the elapsed time of each volumetric infusion pump motor session. In another embodiment, the age of a volumetric infusion pump motor is the elapsed time since a predefined qualifying event. In one embodiment, a predefined qualifying event is a date and time stamp indicating a first usage of a volumetric infusion pump. In another embodiment, a predefined qualifying event is a date and time stamp indicating the date and time of a factory based event, for example, the date and time of construction of the volumetric infusion pump or the date and time of the end of the quality assurance process for a volumetric infusion pump.

In one embodiment, the age of a volumetric infusion pump motor is stored in a database. In one embodiment, the age is associated with an identifier for a specific volumetric infusion pump motor.

Next, at decision step 360, a determination is made whether to modify the electrical current value to account for any changes in torque due to age-related factors such as increases or decreases in friction, tolerances, and the like. These age factors can, if desired, be tailored to the unique manufacturer of the motor. Moreover, any electrical current modification values as discussed above can include a taking into account of the unique characteristics of the motor such as manufacturer and motor specifications.

If a determination is made in step 360 that the electrical current should be modified, then processing continues at step 370. Accordingly, at step 370, the electrical current value is set to a value appropriate to all determined values, including the age of a volumetric infusion pump. In one embodiment, the determination of the current value appropriate to elapsed time is determined by applying an age-dependent algorithm to a current value appropriate to all other determined values. In another embodiment, the determination of the current value appropriate to the age of a volumetric infusion pump is determined by querying a database containing a table relating current values to the age of a volumetric infusion pump. Processing then continues at step 300.

If a determination is made at step 360 that the electrical current should not be modified, then processing continues to step 300. At step 300, current at the current value determined by the method of FIG. 3 is applied to the stepper motor. Finally, at step 310, the method ends.

In yet another embodiment, the electrical current value determined in the method of FIG. 3 is further determined with reference to the voltage provided by a battery within the infusion pump that supplies electrical power to the pump. In an embodiment, the amount of current provided to the motor is modified, an in particular increased, as the voltage potential of the battery falls below a nominal level. Moreover, the amount of current provided to the motor is modified, an in particular decreased, as the voltage potential of the battery rises above a nominal level.

While the specific embodiment has been illustrated and described, numerous modifications come to mind without significantly departing from the spirit of the invention, and the scope of protection is only limited by the scope of the accompanying claims.

What is claimed is:

1. A method for driving an infusion pump motor, the method comprising the steps of:
   determining a position in a pump cycle;
   determining a flow rate; and
   adjusting an electrical current value for driving an infusion pump stepper motor in response, at least in part, to the position in the pump cycle and the flow rate as separate factors, wherein the steps of determining are accomplished at least 200 times per revolution of the stepper motor, and wherein the position in the pump cycle and an expected electrical current value are related to each other in a relational database.

2. The method of claim 1, further comprising adjusting an electrical current value provided by a battery within the infusion pump for driving the infusion pump stepper motor based on a voltage provided by the battery.

3. The method of claim 1, wherein the position in the pump cycle, the flow rate and an expected current value are stored in a database, and wherein the position in the pump cycle and the flow rate are related to the expected electrical current value.

4. The method of claim 1, further comprising a step of modifying the electrical current value in response to input from a temperature sensor.

5. The method of claim 1, further comprising a step of modifying the electrical current value in response to input from a pressure sensor.

6. The method of claim 1, further comprising a step of modifying the electrical current value in response to an elapsed time value.

7. The method of claim 1, further comprising a step of modifying the electrical current value in response to an age of the infusion pump stepper motor.

8. The method of claim 1, further comprising a step of half-stepping the infusion pump stepper motor.

9. The method of claim 1, further comprising the step of microstepping the infusion pump stepper motor.

10. A system for controlling an infusion pump, the system comprising:
a motor controller having an output responsive to a plurality of inputs, the motor controller configured to output an electrical signal and to adjust the electrical signal;
a current driver having an electrical current output responsive to the motor controller electrical signal;
a stepper motor responsive to the electrical current output; and
at least one sensor having an output to the motor controller, wherein the motor controller is configured to determine a position of the motor with respect to the pump cycle or with respect to an output volume of the pump, and wherein a table of an expected electrical current value for a plurality of motor positions or output volumes are stored in a relational database accessible by the motor controller, and wherein the relational database includes a table for an expected electrical current value based upon at least one of an ambient temperature, a backpressure of the fluid pumped by the infusion pump, an age of the motor, and an age of tubing used in the infusion pump.

11. The system of claim 10 further comprising a battery for operating the infusion pump.

12. The system of claim 10 wherein the sensor is a temperature sensor.

13. The system of claim 10 wherein the sensor is a pressure sensor.

14. The system of claim 10 wherein the sensor is responsive to changes in the position of the stepper motor.

15. The system of claim 10 wherein the output of the motor controller is responsive to changes in the age of tubing used for administering medication.

16. The system of claim 10 wherein the output of the motor controller is responsive to changes in the age of the stepper motor.

17. The system of claim 10 wherein the controller and memory are within a microcontroller.

18. The system of claim 10 further comprising a stepper motor position sensor.

19. A system for controlling an infusion pump, the system comprising:
an infusion pump;
a motor controller within the infusion pump, the controller having an output responsive to a plurality of inputs, the motor controller configured to output an electrical signal and to adjust the electrical signal;
a current driver having an electrical current output responsive to the motor controller electrical signal;
a stepper motor within the infusion pump, the stepper motor responsive to the electrical current output; and
at least one sensor having an output to the motor controller, wherein the motor controller is configured to determine a position of the motor with respect to the pump cycle or with respect to an output volume of the pump, and wherein a table of an expected electrical current value for a plurality of motor positions or output volumes is stored in a relational database accessible by the motor controller, and wherein the relational database includes a table for an expected electrical current value based upon at least one of an ambient temperature, a backpressure of the fluid pumped by the infusion pump, an age of the motor, and an age of tubing used in the infusion pump.

20. The system of claim 19, further comprising a battery for operating the infusion pump.

21. The system of claim 19 wherein the sensor is a temperature sensor.

22. The system of claim 19 wherein the sensor is a pressure sensor.

23. The system of claim 19 wherein the sensor is responsive to changes in the position of the stepper motor.

24. The system of claim 19 wherein the output of the motor controller is responsive to changes in the age of tubing used for administering medication.

25. The system of claim 19 wherein the output of the motor controller is responsive to changes in the age of the stepper motor.

26. The system of claim 19 which includes an additional sensor and wherein the output of the additional sensor is responsive to changes in the position of the stepper motor.

* * * * *